United States Patent
Hirao et al.

(10) Patent No.: US 7,326,810 B2
(45) Date of Patent: Feb. 5, 2008

(54) METHOD FOR STARTING UP REACTOR

(75) Inventors: Harunori Hirao, Himeji (JP); Yukihiro Matsumoto, Kobe (JP); Sei Nakahara, Himeji (JP); Kunihiko Suzuki, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/919,024

(22) Filed: Jul. 31, 2001

(65) Prior Publication Data
US 2002/0037488 A1    Mar. 28, 2002

(30) Foreign Application Priority Data
Aug. 7, 2000    (JP) ............................. 2000-238419

(51) Int. Cl.
*C07C 27/10* (2006.01)
*C07C 51/16* (2006.01)
(52) U.S. Cl. .................... 562/512.2; 562/532
(58) Field of Classification Search ............... 560/208; 562/512.2, 532; 431/268
See application file for complete search history.

(56) References Cited
U.S. PATENT DOCUMENTS 3,366,648 A * 1/1968 Kerr ..................... 549/259
3,904,652 A * 9/1975 Frank .................... 549/260
4,203,906 A * 5/1980 Takada et al. ........... 549/248
5,155,242 A    10/1992 Shankar et al. .......... 549/534
5,817,865 A    10/1998 Machhammer et al. ..... 560/208

FOREIGN PATENT DOCUMENTS

| WO | WO 99/20590 | 4/1999 |
| WO | WO 99/31012 | 6/1999 |

* cited by examiner

*Primary Examiner*—Taylor Victor Oh
(74) *Attorney, Agent, or Firm*—Mathews, Shepherd, McKay & Bruneau, P.A.

(57) ABSTRACT

In the reaction of catalytic gas phase oxidation induced by the supply of at least a raw material to be oxidized and a molecular oxygen-containing gas to a reactor for catalytic gas phase oxidation, a method for starting up the reactor for catalytic gas phase oxidation is disclosed which is characterized by causing the raw material and the molecular oxygen-containing gas to pass a range in which the concentration of the raw material is less than the lower explosion limit of the raw material and the concentration of oxygen is not less than the limiting oxygen concentration, but excluding the concentration of the raw material of 0 vol. %. The method enables the reactor to be started up economically and safely by avoiding the explosion range induced by the composition of a raw material and a molecular oxygen-containing gas supplied to the reactor and decreasing the amount of a diluting gas to be supplied.

3 Claims, 4 Drawing Sheets

METHOD FOR STARTING UP REACTOR

BACKGROUND OF THE INVENTION

1. Field of the Invention

This invention relates to a method for starting up a reactor for the catalytic gas phase oxidation to be induced by the supply of a raw material to be oxidized in combination with a molecular oxygen-containing gas, and more particularly to a method for starting up a reactor for the catalytic gas phase oxidation, characterized by causing the raw material and the molecular oxygen-containing gas supplied to the reactor for the purpose of oxidation therein to pass a range in which the concentration of the raw material falls short of the concentration of the lower explosion limit of the raw material and the concentration of the oxygen is not less than the limiting oxygen concentration, excluding the concentration of the raw material of 0 vol. %.

2. Description of Related Art

The (meth)acrylic acid which is a general-purpose monomer is produced by the reaction of catalytic gas phase oxidation of propylene, isobutylene, t-butanol, methyl-t-butyl ether, acrolein, or methacrolein. Since this production consists in the oxidation reaction, it necessitates supply of a molecular oxygen-containing gas in combination with the raw material gas. And the oxidation reaction is generally an exothermic reaction by nature, the reactivity of the raw material gas is largely varied by the property of the catalyst to be used, the concentration of the raw material gas and the molecular oxygen-containing gas, and the conditions for the removal of the heat of reaction. When a general-purpose monomer is to be mass-produced on account of a large demand, therefore, it is important for the purpose of securing the largest possible yield of production to attain the efficient production by setting the optimum reaction conditions in the initial stage of the production of the target compound by the reaction of catalytic gas phase oxidation.

The interior of the reactor for the catalytic gas phase oxidation, however, is a multicomponent system comprising the reaction product in addition to the raw material gas and the molecular oxygen-containing gas. The composition in the reactor changes every moment from the time the reaction is started till the time the steady state is reached. It is generally held that the optimum combination of the three elements, i.e. the property of the catalyst, the property of the explosion range of the reaction gas, and the removal of the heat of reaction, is important for the reaction of catalytic gas phase oxidation. While these three elements are easily maintained after the reaction has reached a steady operation, it is extreme difficult for the elements to control between the time the reaction of catalytic gas phase oxidation starts and the time the reaction reaches the steady state. The reason for this difficulty is that the concentration of the raw material to the interior of the reactor is varied from a low level to a high level, that the amount of the heat generated in consequence of the oxidation reaction is changed in accordance with the fluctuation of the concentration of the raw material, and that the other elements which have direct influences on the reaction of catalytic gas phase oxidation are varied in consequence of variations of the elements mentioned above. From the time of starting the reaction till the time of reaching the steady state, therefore, it is necessary to select within the shortest possible duration such setting conditions as excel in the economy inclusive of the energy of consumption rather by taking account of the time and safety required for enabling the reactor to acquire the steady state, the amounts of the raw material gas and other gas to be used therefor, and the amount of the energy spent for heating the raw material than by paying full attention to the efficiency of the reaction. Moreover, in the reactor for the catalytic gas phase oxidation of a raw material compound for oxidation liable to induce an exothermic reaction prone to explosion, it is extremely important to carry out the reaction under the conditions which warrant safety of a high degree enough to avoid inciting combustion or explosion due to the relation between the raw material and the concentration of oxygen.

Since the explosion range inherent in the reactor for the catalytic gas phase oxidation varies with the temperature, the pressure, and the kind of the inert gas to be used, it is necessary to find the explosion range by a preliminary actual measurement and then proceed to control the reaction so as to avoid the explosion range consequently found. The explosion range of the ordinary reactor for the catalytic gas phase oxidation will be described below with the aid of FIG. 4. In FIG. 4, the horizontal axis is the scale for the concentration of oxygen and the vertical axis the scale for the concentration of a raw material to be oxidized and the hatched part is the explosion range which is formed by mixing oxygen and the raw material. The lowermost concentration of the raw material in the gas composition forming the explosion range is called "the concentration of the lower explosion limit of the raw material to be oxidized" and the lowermost concentration of oxygen in the gas composition forming the explosion range is called "the limiting oxygen concentration", in the specification. With reference to FIG. 4, the point of intersection of these two concentrations in the reactor for the catalytic gas phase oxidation is indicated by the mark ③. When the composition of the feed gas in the steady state is indicated by the mark ① indicating the concentration of the raw material gas to be 4.5 vol. % and the concentration of oxygen to be 10 vol. %, for example, it is safe for the purpose of using the reactor while avoiding the explosion range and easy for the adjustment of the composition of the raw material as well to supply to the reactor a feed gas of the composition through the mark ② in which the concentration of the raw material gas is 0 vol. % and the concentration of oxygen is less than the limiting oxygen concentration. It has been heretofore customary, therefore, to adopt the route in which the concentration of oxygen passes the point ② which falls short of the limiting oxygen concentration regarding oxygen concentration and alter the composition on one straight line of the target composition marked as ①.

When the reactor is started up by the conventional method, however, since the reactor prior to starting the use thereof is filled with air, it is necessary for the purpose of lowering the concentration of the oxygen contained in the gas supplied to the reactor in the range of "less than the limiting oxygen concentration" to supply such so-called diluting gases as nitrogen gas and carbon dioxide gas in a large amount to the reactor and control the concentration of oxygen. Further, the operation of starting up the reactor does not merely reside in one course leading up to the steady state but even embraces in its object the evaluation of the fact that the operations of the reactor and the attached devices thereof are carried out safely and stably. It is, therefore, favorable to supply the same amount of the gas to the reactor during the course of starting up the reactor as when the reactor is in the steady state, with the result that the amount of the diluting gas to be used for controlling the concentration of oxygen will be increased. The use of the diluting gas in a large amount, however, is not economical because this gas is expensive.

Incidentally, the reaction of catalytic gas phase oxidation generally entails a step of absorption which absorbs the target compound included in a reaction gas into an absorbent and, at the same time, separates an discharged gas. The discharged gas which emanates from the absorption column contains nearly no object compound and, after the reaction is started in the reactor, the oxygen concentration in the gas changes lower in consequence of the consumption of oxygen by the reaction. Thus, after starting the reaction, this discharged gas can be recycled to the reactor in the place of the diluting gas with a view to saving the diluting gas to be introduced into the reactor. On the other hand, the control of the concentration of oxygen cannot be attained with the recycled gas prior to the introduction of the raw material to be oxidized. It still requires supply of the diluting gas in a large amount. Even after the introduction of the raw material to be oxidized, the replacement of the diluting gas in a large amount with the recycled gas necessitates changes and adjustments in the relevant flow volumes of such gases and, as an inevitable consequence, elongates the duration of the relevant step and enlarges the amount of the diluting gas to be supplied. In this connection, the method which evades the wide changes in the flow rate by having the reactor displaced in advance with a diluting gas is conceivable. Since this displacement consumes a long time and necessitates supply of the diluting gas in a large amount, this method does not deserve to be rated as an excellent measure of improvement.

All these methods are invariably uneconomical because they require supply of the diluting gas in a large amount and because the diluting gas they use is expensive. There are methods which use steam as a diluting gas. They are likewise unfavorable because they require supply of thermal energy in a large amount for the generation of the steam. An effort to save the diluting gas is likewise at a disadvantage in inevitably entailing an elongation of time.

SUMMARY OF THE INVENTION

The present inventor, as a result of studying elaborately the conditions of the reactor during the course of starting up the operation thereof, has found that by causing the gas containing the raw material supplied to the reactor for oxidation therein to pass the range in which the concentration of the raw material in the composition of the gas is less than the concentration of the lower explosion limit of the raw material and the concentration of oxygen in the gas is not less than the limiting oxygen concentration, it is made possible to decrease the amount of a diluting gas supplied to the reactor and, even when the discharged gas remaining after the absorption of the target compound contained in the formed gas emanating from the reactor is recycled to the reactor, repress the variations of the relevant flow rates, permit prompt startup of the reactor, consequently decrease the number of operation steps and the amount of the diluting gas, and accomplish safe startup of the reactor while enabling the reaction to avoid the explosion range. This invention has been perfected as a result. Specifically, the tasks implied above are accomplished by the following items (1) and (2).

(1) In the reaction of catalytic gas phase oxidation induced by the supply of at least a raw material to be oxidized and a molecular oxygen-containing gas to a reactor for the reaction of catalytic gas phase oxidation, a method for starting up the reactor, characterized by causing the raw material and the molecular oxygen-containing gas to pass a range in which the concentration of the raw material is less than the concentration of the lower explosion limit of the raw material and the concentration of oxygen is not less than the limiting oxygen concentration, but excluding the concentration of the raw material of 0 vol. %.

(2) In the process of production including a step for the reaction of catalytic gas phase oxidation induced by supplying at least a raw material to be oxidized and a molecular oxygen-containing gas to a reactor for catalytic gas phase oxidation and a step of absorption, a method for preparing a feed gas, characterized by supplying the discharged gas obtained at the step of absorption to the reactor thereby causing the concentration of the raw material and the concentration of oxygen to fall in a range in which the concentration of the raw material is less than the concentration of the tower explosion limit of the raw material and the concentration of oxygen is not less than the limiting oxygen concentration, but excluding the concentration of the raw material of 0 vol. %.

By causing the gas supplied to the reactor to pass the range in which the concentration of the raw material in the composition of the gas is less than the concentration of the lower explosion limit and the concentration of oxygen is not less than the limiting oxygen concentration according to the present invention, it is made possible to decrease the amount of the diluting gas supplied to the reactor and the thermal energy for adjusting the diluting gas and shorten the duration of the operation of starting up the reactor.

Further, according to this invention, it is made possible to recycle the gas which has passed the range mentioned above to the reactor, consequently decrease the amount of the diluting gas, allow effective utilization of the gas which has been heretofore discarded, and shorten the duration of the operation of starting up the reactor. The aforementioned effect of this invention can be implemented safely because the gas composition embraced in the explosion range can be avoided.

Figure 2:
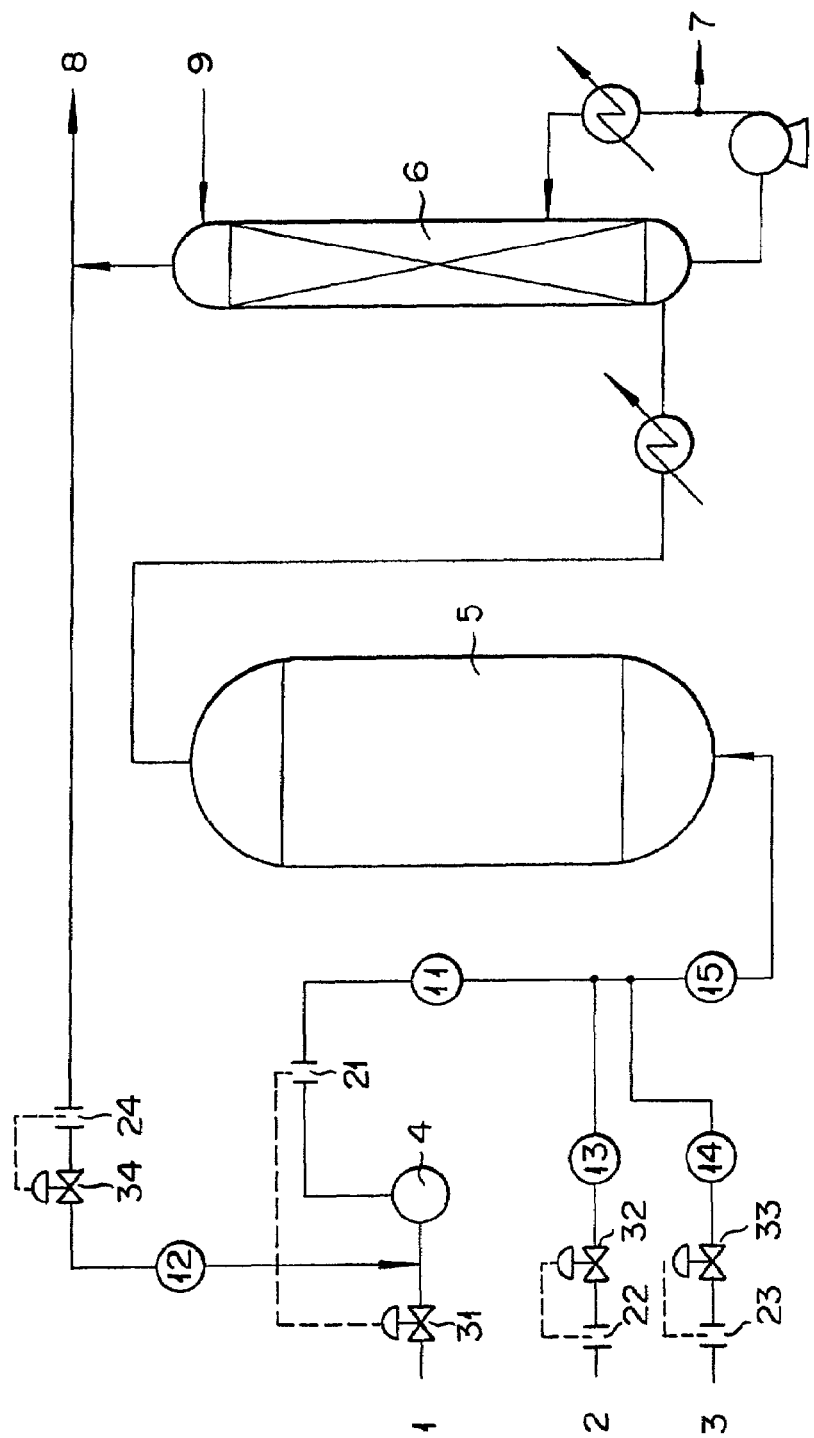
FIG. 2 is a diagram showing the process flow of the method for starting up the reactor of this invention in the operation of producing acrylic acid by the reaction of catalytic gas phase oxidation, then absorbing the acrylic acid with an absorption column, and at the same time recycling a discharged gas obtained from the absorption column to the reactor.

In the diagram of FIG. 2, 1 stands for air, 2 for steam, 3 a raw material to be oxidized, 4 a blower, 5 for a reactor, 6 for an absorption column, 7 for a solution containing the target substance, 8 for a discharged gas, 9 for an absorbent, 11, 12, 13, 14, and 15 each for a position for measuring the flow rate, 21, 22, 23, and 24 each for a flow meter, and 31, 32, 33, and 34 each a flow control valve.

DESCRIPTION OF THE PREFERRED EMBODIMENTS

This invention primarily relates in the reaction of catalytic gas oxidation induced by the supply of at least a raw material to be oxidized and a molecular oxygen-containing gas to the reactor for the reaction of catalytic gas phase oxidation, to a method for starting up the reactor, characterized by causing the raw material and the molecular oxygen-containing gas to pass a range in which the concentration of the raw material in the composition of the gas is less than the concentration of the lower explosion limit of the raw material and the concentration of oxygen is not less than the limiting oxygen concentration, but excluding the concentration of the raw material of 0 vol. %.

Generally in the reaction of catalytic gas phase oxidation, the target compound is formed by gasifying the raw material to be oxidized and supplying the gasified raw material together with the molecular oxygen-containing gas to the reactor which is packed in advance with an oxidation catalyst. The concentration of the raw material to be supplied in the steady state to the reactor is determined by the activity of the oxidation catalyst filling the reactor and the amount of supply of the raw material supplied per unit time. In contrast, during the course of starting up the reactor for catalytic gas phase oxidation, the reaction conditions are varied with the concentration of the raw material, the inner temperature of the reactor, and the temperature of the heat medium for cooling the reactor. It is, therefore, general till the reaction conditions in the steady state are reached to start the supply of the gas containing the raw material from the low level concentration of the raw material in the gas. This invention has originated in the notice taken of the explosion range determined by the relation between the concentrations of the raw material and oxygen in the multicomponent gas supplied to the reactor and culminated in the discovery that by supplying to the reactor a gas of a composition in which "the concentration of the raw material to be oxidized is less than the concentration of the lower explosion limit and the concentration of oxygen is not less than the limiting oxygen concentration," it is made possible to decrease the amount of the diluting gas to be used and the amount of the energy used for adjusting the diluting gas and shorten the duration of the operation of starting up the reactor as well. Now, this invention will be described in detail below.

Figure 1:
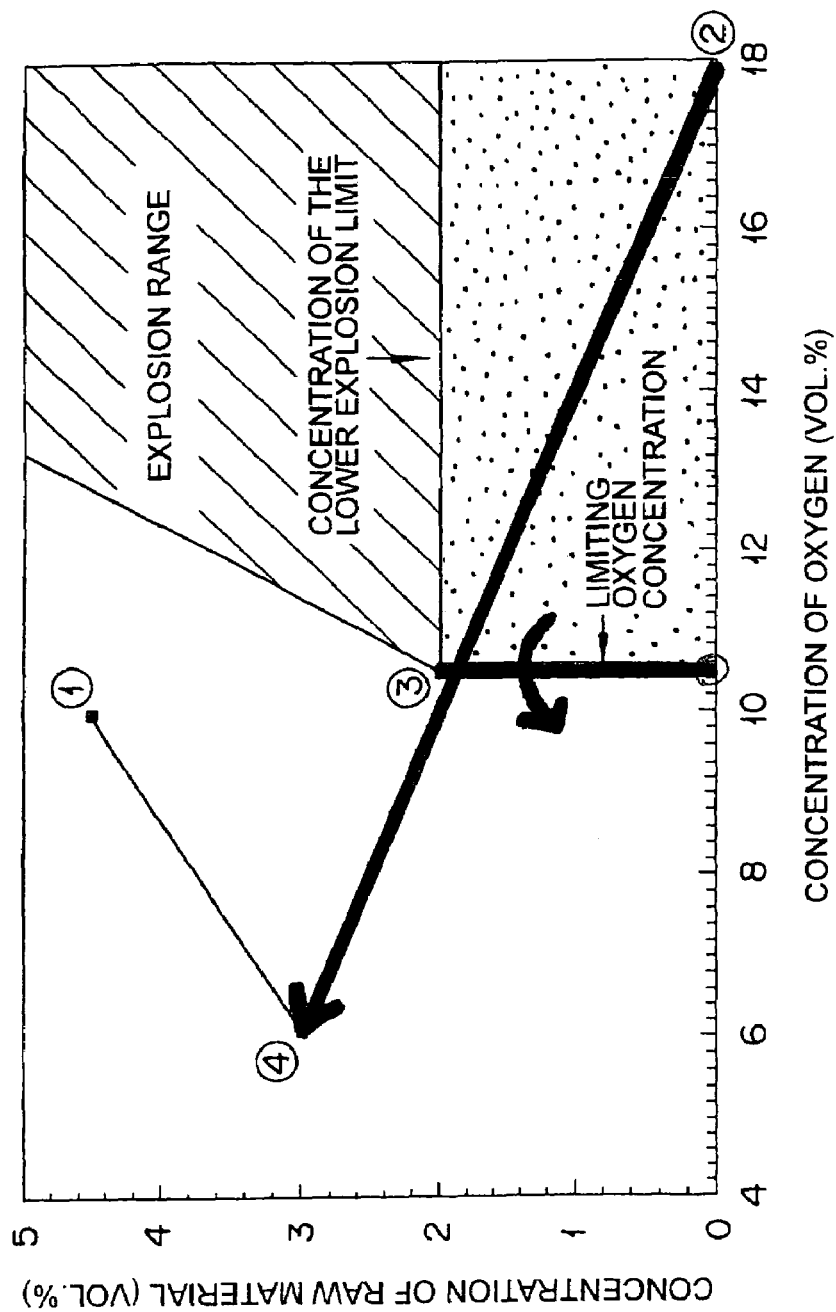
FIG. 1 is a diagram showing the explosion range in the relation between a raw material to be oxidized and the concentration of oxygen in a reactor for the reaction of catalytic gas phase oxidation and a composition of a feed gas supplied to the reactor for starting up according to the present invention.
Figure 4:
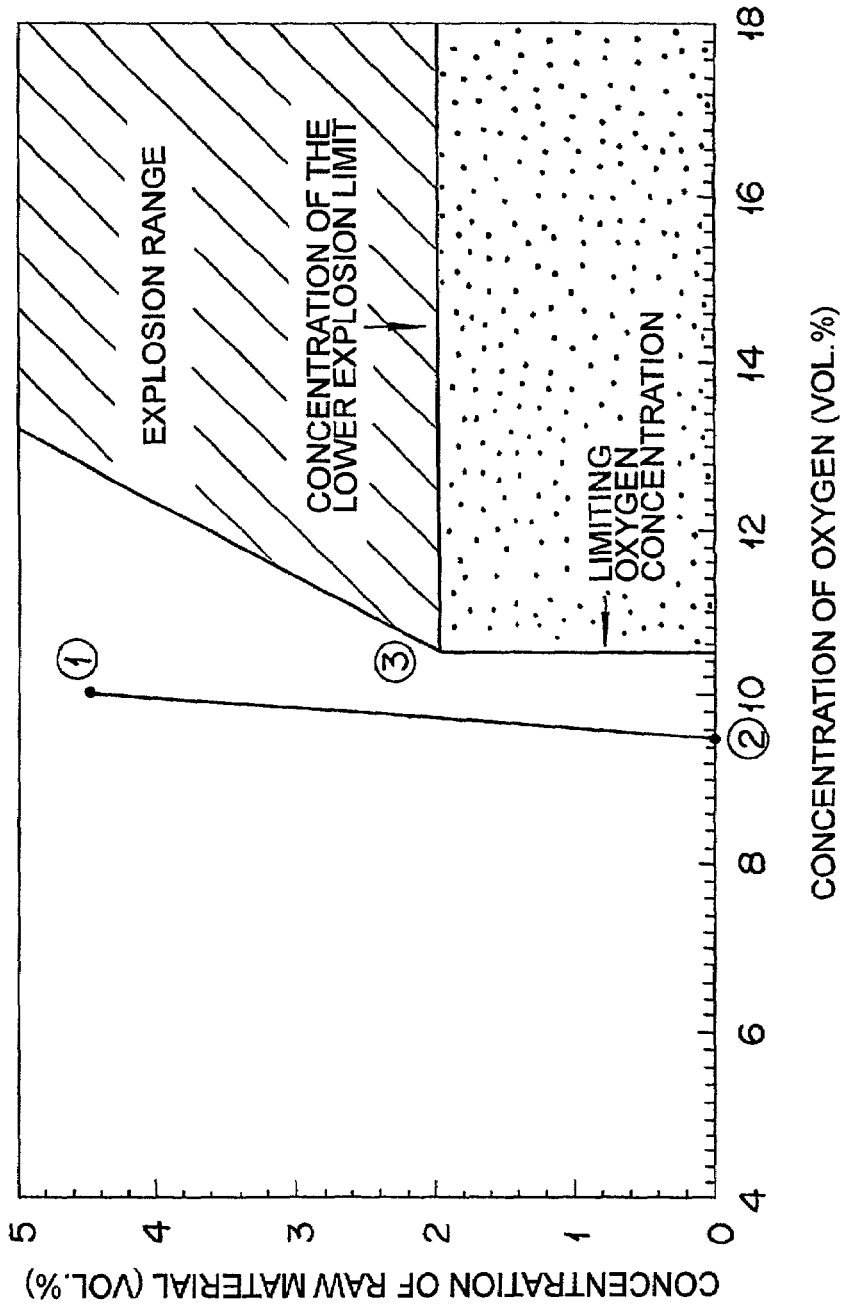
FIG. 4 is a diagram showing the explosion range in the relation between a raw material to be oxidized and the concentration of oxygen in a reactor for the reaction of catalytic gas phase oxidation and a composition of the gas supplied to the reactor for starting up according to the conventional method.

The expression "the range in which the concentration of the raw material supplied to the reactor and used for oxidation therein is less than the concentration of the lower explosion limit of a raw material to be oxidized and the concentration of oxygen supplied to the reactor is not less than the concentration of the limiting oxygen concentration" as used in the present invention will be explained below with the aid of FIG. 1. In FIG. 1, similarly in FIG. 4, the horizontal axis is the scale of the concentration of oxygen and the vertical axis the scale of the concentration of a raw material to be oxidized and the patched part is the explosion range. The expression "the concentration of the lower explosion limit of the raw material" means the lowest possible concentration of the raw material in the composition of the gas forming the explosion range and, by the same token, the expression "the limiting oxygen concentration" means the lowest possible concentration of oxygen in the composition of the gas forming the explosion range. The denomination "vol. %" designates the volume % which is determined at the temperature at which the gases are supplied to the reactor respectively. Incidentally, the explosion range can be found by using an explosion limit measuring device developed by the U.S. Bureau of Mines or an explosion limit measuring device developed by Kitagawa Research Institute.

It is for the purpose of avoiding the explosion range that the concentration of the raw material is specified to be less than the concentration of the lower explosion limit of the raw material. When the concentration of the raw material is less than the concentration of the lower explosion limit, if the concentration of oxygen set arbitrarily, there is no possibility of entering the explosion range. It is for the purpose of decreasing the amount of the diluting gas to be used by heightening the concentration of oxygen that the concentration of oxygen is specified to be not less than the limiting oxygen concentration. The concentration of oxygen is more preferably to be not less than the limiting oxygen concentration and not higher than 20 vol. %. Since the concentration of oxygen contained in the air is about 20 vol. %, the fact that the concentration of oxygen is made to exceed this particular level, 20 vol. %, is rather at a disadvantage in merely resulting in increasing the amount of oxygen to be supplied. In the gas component to be supplied to the reactor, the gas other than the raw material and the molecular oxygen-containing gas will be referred to as "diluting gas" herein. This invention permits use of the conventional gas component as the diluting gas.

In FIG. 1, the composition of the feed gas to be supplied in the steady state to the reactor is indicated by the point ① which represents the concentration of the gas of the raw material, 4.5 vol. %, and the concentration of oxygen, 10 vol. %. In this invention, the gas of the composition having the concentration of the raw material and the concentration of oxygen included in the dotted part of FIG. 1 is supplied to the reactor during the course of starting up the reactor, without reference to the steady state of the reactor. As the gas of the composition falling within this range, the gas of a composition of the point ② which has 0.01 vol. % as the concentration of the raw material and 18 vol. % as the concentration of oxygen, for example, can be supplied to the reactor.

In the composition of the gas supplied to the reactor according to this invention, the gas to be supplied to the reactor has a higher oxygen concentration than the level prevalent conventionally in the composition. Thus, the degree of decrease in the amount of the diluting gas supplied to the reactor becomes extremely large. To be specific, the air which has an oxygen concentration of about 20 vol. % is generally used as the molecular oxygen-containing gas. When the oxygen concentration is set at a conventionally prevalent level of 9 vol. % in the composition of the gas supplied to the reactor, therefore, it becomes necessary to use the diluting gas in compensating the gas for the difference in concentration, x, from the concentration in the air, found by solving the equation, $(20+x)/(100+x)=9/100$, i.e. $x=12.1$ (vol. %). In contrast therewith, this invention, in forming the composition of ②, is only required to use the diluting gas in compensating the gas for the difference, x, found by solving the equation, $(20+x)/(100+x)=18/100$, i.e. $x=2.4$ (vol. %). This invention, therefore, is allowed to decrease the amount of the diluting gas to be used during the course of starting up the reactor to less than one-fifth as compared with the conventional method. Thus, the effect brought about by this invention is extremely large.

Next, for the purpose of effecting a switch to the composition of ①, the amount of the molecular oxygen-containing gas to be supplied is decreased to lower the concentration of oxygen. Further, for the purpose of simultaneously heightening the concentration of the raw material, the amount of the raw material to be supplied for oxidation is increased. Since the amount of the gas supplied per unit time to the reactor is preferred roughly to equal the amount in the steady state, the total amount of the gas is adjusted by increasing or decreasing the amount of the diluting gas to be supplied. It is consequently made possible to attain easy adjustment of the concentration of the gas to be supplied and, at the same time, permit supply of the gas to the reactor in the same amount as during the steady state of the reactor, and rate the conditions of operation of the reactor such as the leakage of the gas from the reactor.

During the course of starting up the reactor, after the composition of the gas supplied to the reactor has passed "the range in which the concentration of the raw material is less than the concentration of the lower explosion limit of the raw material and the concentration of oxygen is not less than the limiting oxygen concentration," this invention allows the concentration of the raw material and the concentration of oxygen to be freely selected within the range not including the explosion range. Subsequently to the composition of ②, for example, the composition is made to reach the point ③ at which the concentration of the raw material is 2 vol. % and the concentration of oxygen 10 vol. %. Thereafter, the composition is adjusted to the point ①, namely the composition of the gas supplied during the steady state to the reactor, in which the concentration of the raw material is 4.5 vol. % and the concentration of oxygen 10 vol. %.

After the point ③ in FIG. 1 has been passed, it is allowed to select the conditions which have a lower oxygen concentration than the conventionally prevalent level as in the composition in which the concentration of the raw material is 3 vol. % and the concentration of oxygen is 6 vol. % (position ④ of composition). Especially when the discharged gas from other step or other plant is utilized as specifically described hereinbelow, the concentration of oxygen may be low, depending on the composition of the discharged gas. Even in this case, the amount of the diluting gas to be used may be lowered below the conventionally prevalent level by making effective use of the discharged gas.

As regards the adjustment of the composition of the gas to be supplied to the reactor, it suffices to increase the amount of the raw material supplied for oxidation for the purpose of heightening the concentration of the raw material, for example, or to decrease the amount of the molecular oxygen-containing gas to be supplied for the purpose of decreasing the concentration of oxygen. For the purpose of fixing the amount of the gas supplied per unit time to the reactor, the amount of the gas may be adjusted by increasing or decreasing the amount of the diluting gas to be supplied.

As described above, this invention attains the decrease in the amount of the diluting gas by clarifying the explosion range existing during the course of starting up the reactor and, particularly with respect to the concentration of oxygen, using the oxygen at a concentration of not less than limiting oxygen concentration. By supplying the gas of a composition falling in this range to the reactor, it is made possible to attain such contraction of the duration of recycling the discharged gas generated at the subsequent step and such decrease in the diluting gas as have never been fulfilled to date. Now, the method for recycling the gas which obtained from the step of producing the target compound by the reaction of catalytic gas phase oxidation will be described below.

Generally, when the raw material is subjected to the reaction of catalytic gas phase oxidation, many kinds of by-products are formed besides the target substance. Thus, the resultant reaction mixture is purified at the subsequent step so isolate the target substance. As a preliminary step to this purification, the target substance in the reaction gas is absorbed into an absorbent and the residue of the gas is discharged from an absorption column. Since the gas discharged at the step of absorption entrains substantially no target compound and also has a low oxygen concentration, it can be effectively utilized in the place of a diluting gas.

The method of this invention for starting up the reactor, as applied to a process of production which includes a step of absorption subsequently to the step of reaction of catalytic gas phase oxidation, is therefore capable of starting up the reactor by supplying to the reactor the discharged gas obtained from this step of absorption in combination with the raw material and the molecular oxygen-containing gas.

As a concrete example of this step of absorption, the step which consists in absorbing at least the target compound from the reaction gas obtained by the reaction of the catalytic gas phase oxidation. For the absorption of the target compound, the method which comprises causing the reaction gas to contact an absorbent for the absorption of the target compound thereby recovering the target compound in the absorbent as well as the method which comprises cooling the reaction gas to a level below the condensing point of the target compound thereby separating the target compound as a solution or a solid is available. The method which brings an absorbent or a gas containing a component capable of reacting with the target compound into contact with the reaction gas thereby attaining separation of a target compound derivative may be used instead. In any event, such methods are invariably required only to separate the component of the reaction gas other than the target compound in the form of a gas. This invention particularly prefers to recycle the gas obtained from the step of absorption which follows the step of performing the reaction of catalytic gas phase oxidation in the process for the production of (meth)acrylic acid. The reaction of catalytic gas phase oxidation of (meth)acrylic acid is exothermic by nature, the gas is heated in advance of being supplied to the reactor to a temperature which fits the property of the catalyst in use. Further, since the gas formed by the reaction has a high temperature, the step of absorption which advances this reaction gas into counter flow contact with the absorbent discharges a gas at a high temperature. Thus, the reclamation of the thermal energy can be attained by using the discharge gas of high temperature emanating from the step of absorption for starting up the reactor.

As one concrete example of the method for recycling the discharged gas from the step of absorption, the method which comprises obtaining acrylic acid by supplying propylene as the raw material to the reactor for the reaction of catalytic gas phase oxidation and supplying the acrylic acid to an acrylic acid absorption column and consequently recovering the acrylic acid in the absorbent and, at the same time, recycling the gas discharged through the top of the absorption column to the reactor for catalytic gas phase oxidation will be described below with the aid of FIG. 2.

In the diagram of FIG. 2, 1 stands for air, 2 for steam, 3 for propylene as the raw material to be oxidized, 4 for a blower, 5 for a reactor for catalytic gas phase oxidation, 6 for an absorption column, 7 for an acrylic acid-containing solution, 8 for discharged gas, 9 for an absorbent, 11, 12, 13, 14, and 15 each for a position for measuring the flow rate, 21, 22, 23, and 24 each for a flow meter, and 31, 32, 33, and

34 each for a flow control valve. The reaction tubes built in the reactor are filled with a catalyst for catalytic gas phase oxidation.

First, at the time of starting the use of the reactor, the interior of the reactor is adjusted to atmospheric pressure with the air which has an oxygen concentration of 20 vol. %. In this invention, the concentration of oxygen at which the air is supplied is controlled with a flow meter and a flow control valve which belong to each of the relevant lines. The concentration of the propylene at which the propylene is supplied as the raw material is set in a range in which the concentration of propylene, vol. %, is less than the lower explosion limit of propylene and the concentration of oxygen, vol. %, is not less than the limiting oxygen concentration. When the amount of the gas supplied per unit time is so set as to equal the amount of the gas in the reactor in the steady state, the concentration of oxygen, the concentration of the raw material, and the amount of the gas supplied per unit time to the reactor can be easily adjusted by controlling the amount of the steam supplied as the diluting gas with the flow meter and the flow control valve attached to the relevant line. Incidentally, the steam is supplied as heated with a heating device (not shown) which is similarly attached.

Next, the gas containing air, steam, and the raw material which has been supplied to the reactor is oxidized with the catalyst occupying the interior of the reactor to form acrylic acid as the target compound. The reaction gas which contains this acrylic acid is supplied to the absorption column. The absorption column, for the purpose of absorbing the acrylic acid obtained from the reactor, introduces the absorbent through the top of the column and advances it into counter flow contact with the acrylic acid containing gas from the reactor. Thereafter, it delivers the acrylic acid solution via the bottom of the column to the subsequent step. The remainder of the gas is discharged through the top of the absorption column. This invention recycles the discharged gas from this absorption column to the reactor. During the course of starting up the reactor, the absorption column possibly fails to operate on account of the insufficiency of the concentration of the raw material supplied to the reactor for oxidation. Even in this case, the gas obtained from the absorption column can be recycled to the reactor. This reclamation warrants effective utilization of the raw material, air, and diluting gas contained in the discharged gas and permits the thermal energy owned by the discharged gas to be recycled. Particularly since the reactor can be safely started up even when the concentration of oxygen is not less than the concentration, vol. %, of the limiting oxygen concentration, the greater part of the discharged gas from the absorption column can be recycled to the reactor and the ratio of recycle of the thermal energy can be exalted to an extremely high degree.

When the discharged gas from the step of absorption is supplied to the reactor and utilized for starting up the reactor, since the composition of the discharged gas from the step of absorption varies with the changes in the concentration of the raw material and the concentration oxygen to be supplied to the reactor, it becomes necessary to analyze the composition of the discharged gas at proper intervals and adjust the amount of each gas supplied to the reactor based on the result of the analysis.

Specifically, the gas to be supplied to the reactor is adjusted so as to assume an optimum composition by the use of a flow meter and a flow control valve provided for each line and a gas component analyzer (not shown) optionally disposed therein. The adjustment of the concentration of propylene as the raw material is controlled with a flow meter and a flow control valve attached to the line for propylene and the adjustment of the amounts of air and steam to be supplied is controlled with a flow meter and a flow control valve similarly provided in the relevant line. Particularly since the discharged gas generated at the step of absorption has the composition thereof varied with the kind, quantity, and temperature of the absorbent, it becomes necessary when the gas is recycled to the reactor to control properly the flow of the raw material and the flow of oxygen through the respective feed lines according to the information on the concentration of the raw material and oxygen in the gas. When it is difficult to control the concentration of the raw material and the concentration of oxygen on account of the quality of the discharged gas, the diluting gas such as steam or nitrogen gas is further supplied for the purpose of adjusting the respective concentrations to the optimum levels and also adjusting the respective amounts of supply per unit time.

In starting up the reactor as contemplated by this invention, the conditions heretofore known to the art may be adopted as the conditions other than the composition of the gas to be supplied to the reactor. The conditions of absorption including the composition, amount of supply, and temperature of the absorbent in the absorption column, the amount of supply and temperature of the reaction gas, and the pressure in the absorption column are such as to permit appropriation of any of the relevant conditions known to the art.

When the method of this invention for starting up the reactor is incorporated in the process for the production of acrylic acid as described above, it is made possible by supplying a gas containing oxygen in a heretofore impracticable concentration to the reactor to cut the amount of the diluting gas to be supplied and the energy to be inevitably spent in adjusting the diluting gas, permit the discharged gas from the absorption column to be utilized without any waste, and consequently decrease the amount of the diluting gas to be used. Further,even when the discharged gas of this nature is recycled, the reactor can be started up safely and promptly.

The method for producing acrylic acid has been described heretofore. It is made possible by using isobutylene instead as the raw material to be supplied to the reactor to produce methacrylic acid.

The reactor for catalytic gas phase oxidation which forms the object of the method of this invention for starting up a reactor does not need to be particularly discriminated on account of the shape of the reactor and the kind of the catalyst used in filling the reactor but is only required to induce the reaction of catalytic gas phase oxidation between a raw material to be oxidized and a molecular oxygen-containing gas through the medium of the catalyst filling the reactor. Thus, a shell-and-tube type reactor having accommodated in the shell thereof a multiplicity of reaction tubes packed with a catalyst may be cited as a concrete example of the reactor under discussion.

Then, the raw material to be oxidized is a raw material which is supplied to the reactor for the purpose of obtaining a target substance or an intermediate thereof by the reaction of catalytic gas phase oxidation. Various compounds can be used as raw materials, depending on the target substances. When acrylic acid, methacrylic acid, acrolein, phthalic acid, and maleic acid are selected as target compounds, for example, propylene, propane, acrolein, isobutylene, methacrolein, xylene, naphthalene, benzene, and butane may be used as the raw materials. Then, air is a typical example of the molecular oxygen-containing gas.

This invention provides a method which is at an unusually high advantage in enabling a reactor to be started up stably, economically, and promptly while retaining the safety of the reactor during the course of starting up the operation thereof.

EXAMPLES

Now, this invention will be described more specifically below with reference to working examples to be adduced herein below.

Example 1

An apparatus for the production of acrylic acid illustrated in FIG. 2 was used. Under the following conditions, a raw material to be oxidized, air, and a discharged gas from an absorption column were recycled to the reactor to initiate a reaction of catalytic gas phase oxidation therein. The reactor was a shell-and-tube type reactor made of steel and measuring 25.0 mm in inside diameter and 29.0 mm in outside diameter and furnished with 11500 reaction tubes. The shell of the reactor was a cylinder 4400 mm in inside diameter. Each of the reaction tubes was packed with 1520 cc of a reaction catalyst.

The reactor was set under target operating conditions, i.e. a concentration, 4.5 vol. %, of propylene and a concentration, 10.0 vol. %, of oxygen at the inlet to the reactor on the condition of avoiding use of a diluting gas other than steam and the recycle gas discharged from an absorption column and then the reactor was started up. By the measurement made prior to the start of the reaction, the concentration of propylene at the lower explosion limit was found to be 2 vol. % and the limiting oxygen concentration was found to be 10.2 vol. % (in the propylene-oxygen-nitrogen system) at the temperature under the pressure both set in advance. The purity of the propylene supplied to the reactor was 99.5 vol. %.

Figure 3:
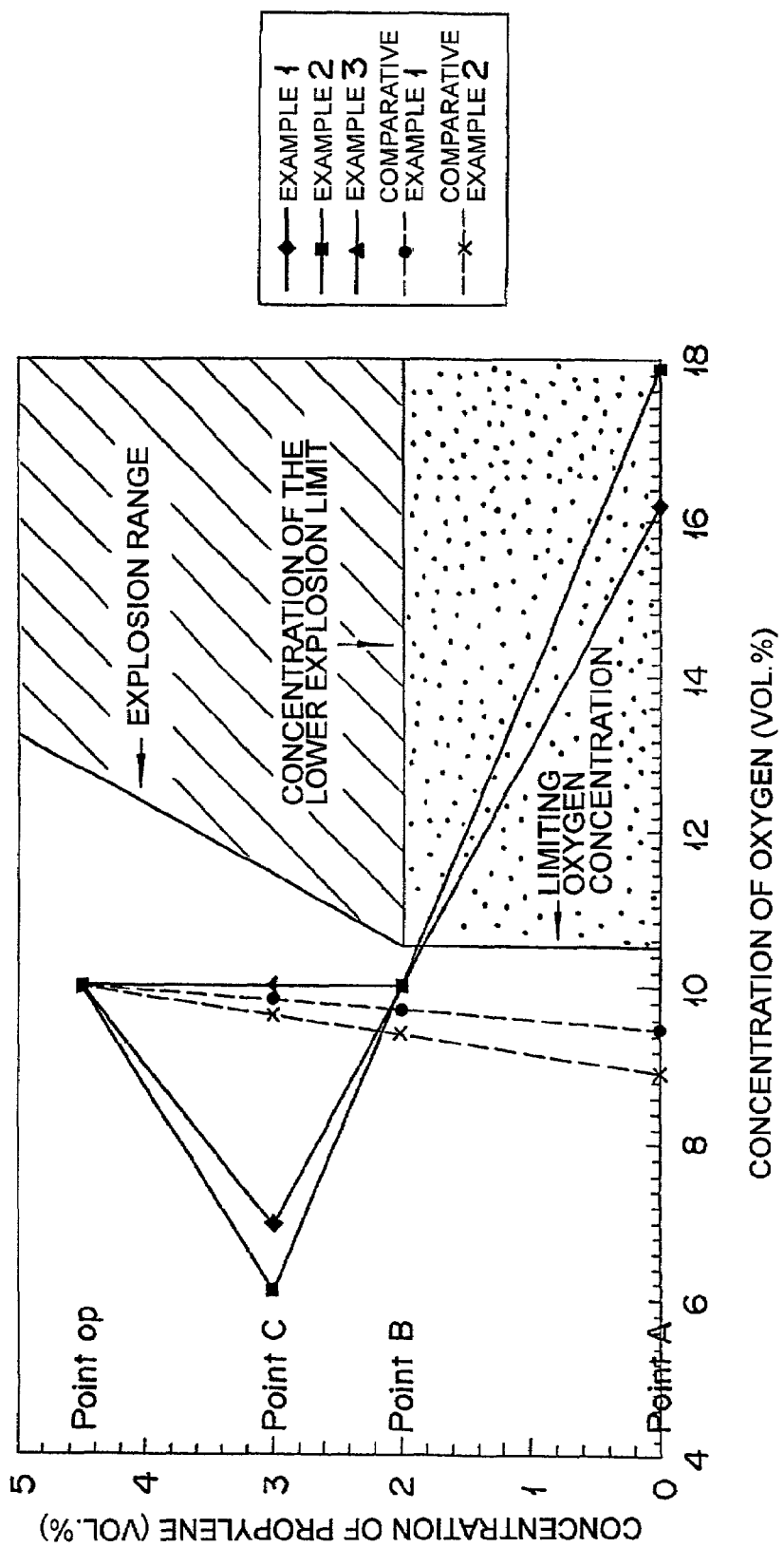
FIG. 3 is a diagram showing the explosion range in the relation between the concentrations of propylene and oxygen in the reactor for catalytic gas phase oxidation and a composition of a feed gas for starting up in the working example.

The concentration of propylene at the inlet to the reactor was gradually increased, A: 0 vol. %, B: 2 vol. %, and C: 3 vol. %, by controlling the flowrate of air, steam, propylene, and discharged recycle gas through their respective lines with flow meters and flow control valves attached to the respective lines and the flow rate of air, discharged recycle gas, steam, and propylene and the concentration of oxygen at the inlet to the reactor necessary for attaining the target operating conditions (OP) were measured at the respective relevant points. The amounts of steam consumed till the points were reached were also measured. The results are shown in Table 1. In this table, the flow rate of air, discharged recycle gas, steam, and propylene and the total flow rate of gas were reported in the denomination of $Nm^3/min$, the concentration of oxygen at the inlet to the reactor was reported in vol. %, and the amount of steam consumed was reported in Kg. Consequently, the amount of steam consumed was found to be about 2.5 tons and the duration of starting up the reactor to be about 2.5 hours. FIG. 3 shows the changes in the concentration of propylene (vol. %) and the concentration of oxygen (vol. %) at the inlet to the reactor found in Examples 1 to 3 and Comparative Examples 1 and 2.

TABLE 1

|   | Flow rate of air* (11) | Flow rate of discharged recycle gas (12) | Flow rate of steam (13) | Flow rate of propylene (14) | Total flow rate of gas (15) | Concentration of oxygen at inlet to reactor | Amount of steam consumed |
|---|---|---|---|---|---|---|---|
| A | 303.0 | 204.1 | 35.0 | 0.0 | 338.0 | 16.2 | 845 |
| B | 296.3 | 206.9 | 35.0 | 6.7 | 338.0 | 10.0 | 1222 |
| C | 293.0 | 201.8 | 35.0 | 10.0 | 338.0 | 6.9 | 1509 |
| OP | 322.9 | 182.2 | 0.0 | 15.1 | 338.0 | 10.0 | 2494 |

*The "Flow rate of air" includes the flow rate of the discharged recycle gas.

Example 2

The reactor was started up by following the procedure of Example 1 while omitting the use of steam as a diluting gas and adjusting the composition of the gas supplied to the reactor with the flow rate of the discharged recycle gas. The results are shown in Table 2. Consequently, the amount of steam consumed was found to be 0 and the duration of starting up the reactor to be about 3.5 hours.

TABLE 2

|   | Flow rate of air* (11) | Flow rate of discharged recycle gas (12) | Flow rate of steam (13) | Flow rate of propylene (14) | Total flow rate of gas (15) | Concentration of oxygen at inlet to reactor | Amount of steam consumed |
|---|---|---|---|---|---|---|---|
| A | 333.8 | 246.8 | 0.0 | 0.0 | 338.0 | 17.9 | 0 |
| B | 331.3 | 248.4 | 0.0 | 6.7 | 338.0 | 10.0 | 0 |
| C | 328.0 | 242.8 | 0.0 | 10.0 | 338.0 | 6.1 | 0 |
| OP | 322.9 | 183.2 | 0.0 | 15.1 | 338.0 | 10.0 | 0 |

*The "Flow rate of air" includes the flow rate of the discharged recycle gas.

Example 3

The reactor was started up by following the procedure of Example 2 while changing the flow rate of the discharged recycle gas at the point C. The results are shown in Table 3. Consequently, the amount of steam consumed was found to be 0 and the duration of starting up the reactor to be about 3.5 hours.

TABLE 3

|    | Flow rate of air* (11) | Flow rate of discharged recycle gas (12) | Flow rate of steam (13) | Flow rate of propylene (14) | Total flow rate of gas (15) | Concentration of oxygen at inlet to reactor | Amount of steam consumed |
|----|------|------|------|------|------|------|---|
| A  | 333.8 | 246.8 | 0.0 | 0.0  | 338.0 | 17.9 | 0 |
| B  | 331.3 | 248.1 | 0.0 | 6.7  | 338.0 | 10.0 | 0 |
| C  | 328.0 | 218.6 | 0.0 | 10.0 | 338.0 | 10.0 | 0 |
| OP | 322.9 | 182.7 | 0.0 | 15.1 | 338.0 | 10.0 | 0 |

*The "Flow rate of air" includes the flow rate of the discharged recycle gas.

Comparative Example 1

The reactor was started up in the same manner as in the conventional method, with the concentration of oxygen kept at less than the limiting oxygen concentration. The results are shown in Table 4. Consequently, the amount of steam consumed was found to be about 23.1 tons and the duration of starting up the reactor to be about 7 hours.

TABLE 4

|    | Flow rate of air* (11) | Flow rate of discharged recycle gas (12) | Flow rate of steam (13) | Flow rate of propylene (14) | Total flow rate of gas (15) | Concentration of oxygen at inlet to reactor | Amount of steam consumed |
|----|------|------|------|------|------|------|-------|
| A  | 183.0 | 150.0 | 155.0 | 0.0  | 338.0 | 9.5  | 3741  |
| B  | 248.3 | 150.0 | 83.0  | 6.7  | 338.0 | 9.7  | 17526 |
| C  | 268.1 | 150.0 | 59.8  | 10.1 | 338.0 | 9.8  | 20191 |
| OP | 322.9 | 182.3 | 0.0   | 15.1 | 338.0 | 10.0 | 23068 |

*The "Flow rate of air" includes the flow rate of the discharged recycle gas.

Comparative Example 2

The reactor was started up by following the procedure of Comparative Example 1 while omitting the operation of recycling the discharged gas from the absorption column during 10 the process of starting up the reactor. The results are shown in Table 5. Consequently, the amount of steam consumed was found to be 37.0 tons and the duration of starting up the reactor to be about 7 hours.

TABLE 5

|    | Flow rate of air* (11) | Flow rate of discharged recycle gas (12) | Flow rate of steam (13) | Flow rate of propylene (14) | Total flow rate of gas (15) | Concentration of oxygen at inlet to reactor | Amount of steam consumed |
|----|------|------|------|------|------|------|-------|
| A  | 148.0 | 0.0   | 190.0 | 0.0  | 338.0 | 9.0  | 4585  |
| B  | 155.5 | 0.0   | 175.7 | 6.7  | 338.0 | 9.4  | 8792  |
| C  | 159.3 | 0.0   | 168.5 | 10.1 | 338.0 | 9.7  | 10786 |
| OP | 322.9 | 182.6 | 0.0   | 15.1 | 338.0 | 10.0 | 36796 |

*The "Flow rate of air" includes the flow rate of the discharged recycle gas.

The invention claimed is:

1. In the reaction of catalytic gas phase oxidation induced by the supply of at least a raw material to be oxidized and a molecular oxygen-containing gas to a reactor for the reaction of catalytic gas phase oxidation, a method for starting up the reactor characterized by (i) during starting up the reactor causing said raw material and said molecular oxygen-containing gas to have a range in which the concentration of said raw material is less than the concentration of the lower explosion limit of said raw material and the concentration of oxygen is not less than the limiting oxygen concentration corresponding to the lowest concentration of oxygen forming an explosion range and passing across a border line where the concentration of oxygen is the limiting oxygen concentration, but excluding the concentration of said raw material of 0 vol. %, said raw material being selected from the group consisting of propylene, propane, acrolein, isobutylene, methacrolein, xylene, naphthalene and, benzene and (ii) then for reaching steady state causing a range in which the concentration of said raw material is not less than the concentration of the lower explosion limit of said raw material and the concentration of oxygen is less than the limiting oxygen concentration, thereby reaching the steady state.

2. A method according to claim 1, wherein the process of production including a step of absorption subsequently to the step for the reaction of catalytic gas phase oxidation requires the discharged gas emanating from said step of absorption to be supplied to said reactor in combination with said raw material and said molecular oxygen-containing gas.

3. In a process of production including a step for the reaction of catalytic gas phase oxidation induced by supplying at least a raw material to be oxidized and a molecular oxygen-containing gas to a reactor for catalytic gas phase oxidation and a step of absorption, said raw material being selected from the group consisting of propylene, propane, acrolein, isobutylene, methacrolein, xylene, naphthalene, benzene, and butane, a method for preparing said feed raw material, characterized by supplying the discharged gas obtained at said step of absorption to said reactor thereby causing the concentration of said raw material and the concentration of oxygen to fall in a range in which the concentration of said raw material is less than the concentration of the lower explosion limit of said raw material and the concentration of oxygen is not less than the limiting oxygen concentration corresponding to the lowest concentration of oxygen forming an explosion range, but excluding the concentration of said raw material of 0 vol. %.

* * * * *